United States Patent [19]

Mansour et al.

[11] Patent Number: 4,693,972
[45] Date of Patent: Sep. 15, 1987

[54] COMPOSITION AND METHOD FOR RAPID DETECTION OF MICROORGANISMS IN CLINICAL SAMPLES

[75] Inventors: James D. Mansour, Raleigh; Thomas H. Schulte, Cary; Vernon R. Neece, Durham, all of N.C.

[73] Assignee: Becton, Dickinson and Company, Franklin Lakes, N.J.

[21] Appl. No.: 571,001

[22] Filed: Jan. 16, 1984

[51] Int. Cl.$^4$ .................. C12Q 1/04; C12Q 1/44; C12Q 1/02; C12Q 1/06; G07K 3/00; G01N 21/64
[52] U.S. Cl. ........................ 435/34; 435/19; 435/29; 435/39; 435/269; 250/461.2
[58] Field of Search ............ 435/19, 34, 29, 820, 435/4, 253, 259, 264, 269; 424/3, 7.1; 436/63, 94, 172, 174, 175, 177; 250/461.2

[56] References Cited

U.S. PATENT DOCUMENTS

| | | | |
|---|---|---|---|
| 3,445,339 | 5/1969 | Controni et al. | 435/34 |
| 3,917,510 | 11/1975 | Kitamura et al. | 435/259 |
| 4,025,306 | 5/1977 | Studer | 436/177 |
| 4,038,143 | 7/1977 | Juni | 435/34 X |
| 4,094,745 | 6/1978 | Scholefield | 435/39 |
| 4,131,512 | 12/1978 | Dorn | 435/30 |
| 4,225,669 | 9/1980 | Melnick et al. | 435/29 |
| 4,225,783 | 9/1980 | Palin et al. | 435/29 X |
| 4,481,294 | 11/1984 | Downs | 435/259 |
| 4,508,821 | 4/1985 | Mansour et al. | 435/34 |
| 4,622,298 | 11/1986 | Mansour et al. | 435/34 |

OTHER PUBLICATIONS

Zierdt, J. Clin. Microbiol., vol. 15, No. 1, pp. 172-174, Jan. 1982.
Pollock, The American Journal of Medicine, pp. 79-84, Jul. 28, 1983.
Dorn et al., J. Clin. Microbiol., vol. 3, 258-263, Mar. 1976.
Kronvall et al., Acta. Path. Microbiol. Scand. Sect. B, 85:249-254, 1977.
McCarthy et al., J. Clin. Microbiol., vol. 11, 281-285, Mar. 1980.
Good et al., Biochemistry, vol. 5, No. 2, pp. 467-477, Feb. 1966.

Primary Examiner—Esther M. Kepplinger
Assistant Examiner—Shawn P. Foley
Attorney, Agent, or Firm—Richard E. Brown

[57] ABSTRACT

A method for rapid detection of microorganisms in a body fluid sample includes detecting the microorganisms after treatment of the sample with a lysing agent in order to dissolve sample components other than microorganisms, and staining with a fluorescent dye. The lysing agent may be part of a composition which includes a culture medium thereby providing simultaneous lysis and growth before staining. Detection is preferably accomplished by reliance on the fluorescence emitted by the dye having been properly excited by light energy.

A composition suitable for use in the above-described method includes a growth medium and a lysing agent.

18 Claims, No Drawings

COMPOSITION AND METHOD FOR RAPID DETECTION OF MICROORGANISMS IN CLINICAL SAMPLES

BACKGROUND OF THE INVENTION

1. Field of the Invention

This invention relates to the detection of microorganisms. More particularly, it relates to the detection and enumeration of microorganisms in body fluid samples by staining of the microorganisms, subsequent to treatment of the sample with an agent which causes lysis of other components in the sample, so that only the microorganisms are stained. The present invention further relates to a composition, for the above-defined uses, which facilitates simultaneous growth and lysis of components of the sample.

2. Description of the Prior Art

In healthy individuals, most body fluids, such as blood, cerebrospinal fluid or synovial fluid, are sterile, and the presence of microorganisms in these fluids indicates a health problem which, in some cases, may be life threatening. Successful treatment of blood infections requires early diagnosis and proper treatment cannot be initiated until accurate identification of the pathogen has been accomplished. This is made very difficult in the early stages of the infection because the concentration of the pathogen in the blood is very low.

Urine, in contrast, is not a sterile fluid, and microorganisms are present at all times, even in healthy people. Nevertheless, urinary tract infections, generally referred to as bacteriuria, are a major health problem, and there has been considerable debate about what urinary microorganism levels indicate infection and what levels are normal. A review of this subject in light of conventional methods of urinalysis has been presented by Pollock (Am. J. Medicine, Proceedings of a Symposium on Body Fluids and Infectious Diseases, p. 79, July 28, 1983).

For detection of microorganisms in the blood, a variety of systems have been proposed. Two procedures are currently in use in hospital microbiology laboratories. One is a conventional blood culturing method wherein a growth medium is innoculated with the patient's blood and an increase in turbidity, indicative of growth, is monitored over a period of time. The length of time required for growth to result in turbidity is a severe disadvantage. Some organisms require up to 7 days for detection by turbidity.

A second hospital technique is an automated radioisotope detection method wherein the conversion of radioisotope $^{14}C$ labeled nutrients to $^{14}C$ labeled $CO_2$ by growth of microorganisms is monitored in the head space gas. This method has been shown to be able to detect 30% of the positive blood cultures in 12 hours and 70% by 24 hours, but is also dependent on growth for detection. Although detection is accomplished sooner than with conventional culturing methods, the 12-24 hour period involved is still a serious drawback where rapid detection of the pathogen is important.

Other methods have been proposed for the rapid detection of septicemia or bacteremia. Some methods have employed various density gradients in an effort to separate the microorganisms from as many blood cell components as possible. Exemplary of these methods is that disclosed in U.S. Pat. No. 4,131,512 to Dorn wherein a lysed blood sample is deposited on a high density liquid cushioning agent and subjected to centrifugation to cause collection of microbial pathogens at the interface between the cushioning agent and the sample. The collected microbial pathogens are then removed from the cushion and cultured on various nutrient agar plates for colony formation.

Current methodology used in the clinical laboratory for the detection of bacteriuria (generally defined as a concentration of microorganisms in the urine of $1 \times 10^5$ colony forming units per ml (cfu/ml or greater) likewise involves growth-based methods. In these procedures, aliquots of urine (usually 1-10 ul) are cultured for 18-24 hours onto various agar type surfaces and the colonies are counted. These procedures have the disadvantages of the time required for culturing and the cost of materials used on samples which ultimately prove negative.

Staining techniques have also been used for the detection of microorganisms in both blood and urine, and a variety of standard agents such as Gram, Wright, Jenner-Giemsa, Leishman, or May-Grunwald-Giesma stains have been used. For urine samples, these methods have shown a high correlation between uncentrifuged Gram-stained smears and significant bacteriuria. About 90 percent of urine specimens with positive Gram stains have $10^5$ cfu/ml or greater. In addition, a high correlation exists between the presence of bacteria on centrifuged wet mounts used in urinalysis, provided the time lag between collection and examination is not overly long. These methods, although good for Gram-positive infections, may not be sufficient for Gram-negative infections, which may be significant at the $10^4$ cfu/ml level or in symptomatic patients with $10^2$ to $10^4$ cfu/ml.

U.S. Pat. No. 4,025,306 to Studer discloses a method whereby microfilariae in the blood are detected by lysis of the blood cells with formaldehyde, staining with a non-fluorescent dye, and observation microscopically. These organisms are the prelarval stage of threadlike worms which invade body cavities and fluids, and are multicelled in contrast to the essentially single celled microorganisms.

Fluorescence microscopy has been used in a variety of inexpensive staining protocols. For example, açridine orange has been utilized to selectively stain bacteria in various clinical samples, including blood and urethral secretions (L. R. McCarthy and J. E. Senne, J. Clin Microb, 11 281 (1980); G. Kronvall and E. Myhre, Acta Path. Microb. Scand 85, 249 (1977). Ethidium bromide has been used extensively to stain both eukaryotic and prokaryotic cells. However, these methods stain not only the microorganisms, but also the white cells and, to a certain extent, other blood components such as platelets and red blood cells. The presence of these other stained bodies makes it difficult not only to locate the microorganisms (which are normally present in small numbers) but also to differentiate between the microorganisms and other stained white cell components and debris.

Accordingly, there is a need for a better method for the rapid detection of microorganisms in body fluid samples. The present invention fulfills this need.

SUMMARY OF THE INVENTION

In accordance with the present invention microorganisms in body fluid samples are detected by staining with a fluorescent dye after treatment of the sample with an agent which causes lysis of other components present in the sample as, for example, blood cell components. (The term lysis, as used herein, refers to the disintegration of cells by an alteration of the chemical environment or by means of a specific agent.) The method is applicable to most microorganisms. The microorganisms are the only elements which stain and detection becomes possible much sooner than by conventional culturing or staining techniques.

For some samples, the staining can be done directly on the lysed sample. For other samples where the bacterial count/ml in the original sample is very low, limited growth may be performed. For this embodiment, the lysing agent may be added after the growth, or, preferably a composition in which the lysing agent is combined with the growth medium may be used. The sample, when added to this composition, undergoes simultaneous growth of the microorganisms and lysis of sample components other than microorganisms.

Consistent with the present invention, microorganisms at concentrations as low as 10 cells per milliliter of sample are detected in a period of less than about two hours, often in 45 minutes. Radioactive components need not be used, and only one vial is required for analysis of the sample, in contrast to conventional methods which require one vial for growth under aerobic conditions and a second vial for growth under anaerobic conditions.

DETAILED DESCRIPTION OF THE INVENTION

According to the present invention, microorganisms in a body fluid sample are detected by staining with a fluorescent dye after treatment of the sample with a lysing agent to cause disintegration of other sample components which might stain and thereby interfere with enumeration of the microorganisms. Microorganisms which can be detected in accordance with the present invention include, but are not limited to, *Staphylococcus aureus, Escherichia coli, Streptococcus fecalis, Staphylococcus epidermidis, Proteus mirabilis, Pseudomonas aeruginosa, Bacteroides fragilis, Klebsiella pneumoniae, Haemophilus influenzae* and *Neisseria meningitidis.* The microorganisms to be detected and enumerated may be present in any body fluid, as, for example, blood, urine, cerebrospinal fluid, synovial fluid, pleural fluid, and the like.

A suitable body fluid sample for illustrating various features of the invention can be provided by adding microorganisms to be stained and thereby detected to a body fluid sample prior to lysing and staining. The microorganisms can be grown in any suitable medium as for example, trypticase soy broth, and removed during the log growth phase. A quantity of cells, from about $10^3$ to $10^8$, preferably about $10^6$, are washed with saline, suspended in normal saline, and the suspension mixed thoroughly with the sample fluid in a ratio of 1 volume part of microorganism cell suspension and from about 5 to about 100 volume parts of sample. Preferably a 1 volume percent suspension is used. When using a blood sample, whole blood or whole blood pretreated with an anticoagulant, such as heparin, ethylenediamine tetraacetic acid (hereinafter referred to as EDTA) or with sodium polyanethol sulfonate (hereinafter referred to as SPS), can be used.

The mixture of microorganisms and sample fluid is then treated with a lysing agent. The lysing agent is selected to perform lysis of other components of the sample in a controlled manner so that the resulting debris from lysis has a maximum particle size of less than about 0.2 microns, preferably less than about 0.1 micron. At the same time the lysis must not be so severe that the microorganisms to be detected also undergo lysis. It has been determined that use of an enzyme preparation which primarily has protease activity but which also has some nuclease and lipase activity is suitable for effecting lysis in accordance with the invention. Suitable lysing reagents include Zierdt's lysing reagent (0.5% of an enzyme preparation sold under the trade name Rhozyme 41 by Corning Glass Works, Corning, N.Y., in 0.01 molar sodium phosphate buffer, pH 8.0, containing 0.7% Tween 20 polyoxyethylenesorbitan monolaurate—Journal of Clinical Microbiology 15: 172–174, 1982) and a lysing reagent, hereinafter called 5XLA, consisting of 2.5% Rhozyme 41 in 0.01 molar N-[tris(hydroxymethyl)methyl]glycine buffer, pH 8.5, containing 4% Tween 20.

The lysing agent may be added directly to the sample. The amount of lysing agent to be used may be from about 1 to 20 volume parts based on the amount of sample. When using Zierdt's reagent, about 8–10 volume parts of lysing solution is used. When using the preferred 5XLA lysing agent, from about 1 to about 5 volume parts of lysing solution are used.

If growth of the microorganisms in the sample is desired before staining, two alternative growth methods may be used. In the first, a standard culture medium is inoculated with the sample. Any standard culture medium may be used, as, for example, trypticase soy-broth, Columbia broth, brain heart infusion, peptone broth and BACTEC media (Becton Dickinson and Company, Johnston Laboratories Division, Cockeysville, Md.). Limited growth is induced by incubation for from about ½ hour to about 12 hours. In most cases, an incubation period of about 1½ hours provides a bacterial count sufficient for detection. The lysing agent is then added and incubation to allow lysis to take place is carried out as hereinafter described.

In the second growth embodiment, a composition combining the lysing agent and the blood growth medium is inoculated with the sample. The composition contains from 70 to 90% by volume of the medium and 10 to 30% by volume of the lysing agent. In a preferred composition, 80% by volume of trypticase soy broth is mixed with 20% by volume of the lysing agent. The sample is added to this composition in a volume concentration of from about 5 to about 20%, preferably about 10%.

After addition of the lysing agent or the lysing agent-growth composition, the sample is incubated for from about 10 minutes to about 6 hours to allow lysis or lysis and growth to take place. The incubation may be carried out at a temperature of from about ambient to about 50° C. Lysis proceeds faster at higher temperatures, and preferably is carried out at from about 40° to 45° C., preferably 42° C.

After incubation, the lysed sample is stained with a fluorescent dye. Exemplary of fluorescent dyes which may be used are acridine orange, thioflavin T, DAPI or, preferably, ethidium bromide. The stain is added to the sample as a 0.001% aqueous solution. (All percentages used herein are by weight, unless otherwise indicated). The amount of dye to be added will be determined by the microorganism and the sample being used, and in general, the final concentration of dye may be varied from about 1 to about 1000 ug per ml of final volume, preferably from about 2.5 to about 100 ug per ml.

Staining is best accomplished in the presence of a buffer which acts as a staining enhancer. A variety of buffers are known which enhance dye absorption by cells. Exemplary of such buffers is an aqueous composition comprising sodium borate, EDTA, formaldehyde and a surface active agent such as Triton-X-100 (trademark of Rohm and Haas Co. for octyl phenoxy polyethoxyethanol). In a preferred embodiment, these components are present in the buffered sample in final concentrations of 40 mM, 24 mM, 0.02% by volume and 0.02% by volume respectively.

The buffered sample mixture containing the dye is allowed to stand briefly. Observation of the stained cells, as hereinafter described, may be made directly on the buffered and stained sample, or, optionally, the stained cells may be separated from the sample before observation by any conventional separation technique, preferably by centrifugation. In the latter embodiment, the cells are centrifuged against a liquid cushioning agent, such as a fluorinated hydrocarbon. Exemplary of such fluorinated hydrocarbons are those sold under the trade name FLUORINERT by the 3M Company of Minneapolis, Minn. After centrifugation, the supernatant is discarded, and the cells are suspended in saline.

The cells may be observed by detection of fluorescence emission. Approximately 0.01 ml is withdrawn and spread over a microscope slide and observed for from about 1 minute to about 1 hour. The wavelength of the light used for excitation depends on the dye used. For the preferred dye, ethidium bromide, a suitable excitation wavelength is 515 nm, and a suitable emission wavelength is 580 nm.

Analysis may also be carried out by fluorescence activated flow cytometry. This procedure is particularly advantageous for detection and quantitation when the microorganisms are present at low levels. In this technique, cells are passed, one at a time, through the focused beam of a light source, such as a laser, whereby they are caused to emit fluorescent signals which are detected. In the present invention, the lysed and stained sample fluid is passed through the beam of a FACS IV cell sorting instrument, (FACS Division of Becton, Dickinson and Company, Sunnyvale, Calif.) at a rate of from about 0.05 ml/min to about 0.3 ml/min, preferably from about 0.1 ml/min.

The following examples are provided to further illustrate the invention but are not to be construed in any way as limiting the scope of the invention.

EXAMPLE 1

A sample of whole blood pretreated with SPS was divided into 4 aliquots of 0.1 ml each and placed in test tubes. Two of the tubes were treated with 10 ul of normal saline containing $2.74 \times 10^4$ cfu of E. coli. The other two tubes served as controls.

To each tube was added 0.9 ml of Zierdt's lysing reagent and the tubes were incubated at 37° C. for 30 min. A 0.7 ml aliquot of sample was removed from each tube and treated with 100 ul of ethidium bromide and 200 ul of staining buffer.

To one set of tubes (test and control) was added 100 ul of FLUORINERT, the tubes were centifuged, the supernatant discarded and the pellet resuspended in 0.7 ml of normal saline. All tubes were then analyzed on the fluorescence activated flow cytometer. The control and test washed samples were found to contain 985 and $2.2 \times 10^4$ events/ml respectively. The latter represents approximately 80% recovery of the reference method count ($2.7 \times 10^4$ cfu/ml).

EXAMPLE 2

In the same way as described in Example 1, 1 ml of a blood sample was spiked with about $10^8$ cfu of a mixed bacterial culture suspended in 0.1 ml of normal saline, treated with 1.8 ml of Zierdt's reagent, and incubated at 37° for 15 min.

An aliquot of 0.35 ml was stained directly with ethidium bromide in staining buffer. A second aliquot of 0.70 ml was washed by adding 0.1 ml of FLUORINERT, centrifuging and resuspending in normal saline before staining.

When viewed under the microscope, it was seen that only the bacteria were stained in both the washed and unwashed samples. Staining was very bright, but brighter for the unwashed sample.

EXAMPLE 3

In a manner similar to that described in Example 1, five aliquots of 1 ml each of blood previously anticoagulated with EDTA were prepared by serial dilution with the following cfu of E. coli:

| | |
|---|---|
| 1 | $4 \times 10^5$ |
| 2 | $4 \times 10^4$ |
| 3 | $4 \times 10^3$ |
| 4 | $4 \times 10^2$ |
| 5 | control |

A sample (0.2 ml) of each aliquot was removed and mixed with 1.8 ml of Zierdt's reagent in a tube. All tubes were incubated for 30 minutes at 37° C. Two 0.7 ml aliquots were removed from each tube and stained with 100 ul ethidium bromide and 200 ul of staining buffer. One set of tubes was washed with normal saline by centrifugation and resuspended in normal saline. The other was left unwashed. Analysis of the washed samples on the fluorescence activated flow cytometer gave the following recovery of cfu/ml:

| Inoculum (cfu/ml) | Recovery (events/ml) |
|---|---|
| $4 \times 10^5$ | $1.4 \times 10^5$ |
| $4 \times 10^4$ | $1.7 \times 10^4$ |
| $4 \times 10^3$ | $3 \times 10^3$ |
| $4 \times 10^2$ | $1.3 \times 10^2$ |
| control | 1142 |

EXAMPLE 4

An experiment similar to example 3 was performed using whole blood anticoagulated with SPS. Samples (0.3 ml) of blood (tests and control) were incubated with 0.3 ml of lysing reagent (5XLA) for 60' at 42° C. Aliquots (0.5 ml) of these samples were then stained with ethidium bromide and staining buffer for 15' at R.T. Analysis of the washed samples on the fluorescence activated flow cytometer resulted in the following:

| Inoculum (cfu/ml) | Recovery (events/ml) |
|---|---|
| $1.4 \times 10^6$ | $1.27 \times 10^6$ |
| $1.4 \times 10^4$ | $8.3 \times 10^3$ |
| $1.4 \times 10^3$ | $1.68 \times 10^3$ |
| $1.4 \times 10^2$ | $1.64 \times 10^2$ |
| 14 | 49 |
| control | 16 |

EXAMPLE 5

In this example, blood from control and *E. coli* (bacteremia) infected rabbits was used. One ml aliquots of SPS anticoagulated blood from test and control animals were incubated with 1 ml of 5XLA lysing reagent for 60 minutes at 42° C. Ethidium bromide (0.4 ml) and 1.6 ml of staining buffer were then added for 15 minutes at R.T. Fluorinert (0.5 ml) was added and the mixtures were centrifuged at $9,000 \times g$ for 10 minutes. The supernatants were discarded, the pellets resuspended in 2 ml of normal saline, and the suspensions analyzed on the fluorescence-activated flow cytometer. The results are summarized in the following table:

| SAMPLE | COLONY FORMING EVENTS/ML | DETECTED EVENTS/ML |
| --- | --- | --- |
| Control #1 | 0 | 0 |
| #2 | 0 | 6 |
| #3 | 0 | 0 |
| #4 | 0 | 6 |
| #5 | 0 | 0 |
| Test #1 | $1.4 \times 10^4$ | $5.2 \times 10^4$ |
| #2 | $2.3 \times 10^4$ | $2.0 \times 10^5$ |
| #3 | 0 | 152 |
| #4 | 0 | 388 |
| #5 | 10 | 84 |

EXAMPLE 6

*Klebs. pneumoniae*, *Staph. saprophyticus* and *Proteus mirabilis* were grown in trypticase soy broth to mid-log growth phase, the cells were isolated, washed and suspended in normal saline to a final concentration of about $1 \times 10^8$ cfu/ml. A 10 ul volume of each cell suspension was then added to a tube containing 1 ml of sterile filtered urine. Each tube then received 1 ml of 5XLA lysing agent, and all tubes were incubated for 20 min. at 42° C. Staining buffer (1.6 ml) and 0.4 ml of ethidium bromide were added to each tube and all tubes were left for 10 min. at room temperature. Inoculum counts were determined by pour plates, and organism counts determined on the FACS IV fluorescence activated flow cytometer. Microorganism recoveries for this experiment are given in the following table:

| Inoculum, cfu/ml | Recovery events/ml | % |
| --- | --- | --- |
| K. pneumoniae $1.66 \times 10^6$ | $1.8 \times 10^6$ | 108 |
| St. saprophyticus $2.26 \times 10^6$ | $2.1 \times 10^6$ | 93 |
| P. mirabilis $1.76 \times 10^6$ | $8.8 \times 10^5$ | 50 |

EXAMPLE 7

One ml of sterile filtered urine was inoculated with about $1 \times 10^4$ cfu of *Staph. aureus, Staph. saprophyticus, Proteus mirabilis, E. coli, Klebs. pneumoniae* and *Strep. faecalis*. Each tube was treated with 1 ml of 5XLA lysing agent and was incubated for 30' at 42° C. Staining buffer (1.6 ml) and 0.4 ml of ethidium bromide were then added and the tubes were incubated at room temperature for 15'. FACS IV analysis was then performed and percent recovery was determined by comparison to the viable cell count obtained by pour plate.

| Organism | FACS IV % Recovery |
| --- | --- |
| Staph. aureus | 86 |
| Staph. saprophyticus | 142 |
| Proteus mirabilis | 63 |
| E. coli | 100 |
| Klebs. pneumoniae | 94 |
| Strep. faecalis | 126 |

EXAMPLE 8

Urine specimens were obtained from eight asymptomatic control donors. Viable cell counts were obtained by pour plate. A 1 ml aliquot of each control urine was incubated with 1 ml 5XLA lysing agent for 30' at 42° C. Staining buffer (1.6 ml) and 0.4 ml of ethidium bromide were then added and the tubes were incubated for 15' at R.T. FACS IV analysis was then performed and the number of detected events/ml compared to the viable cell count (cfu/ml). Results were the following:

| Sample Donor | CFU/ML | FACS IV Events/ML |
| --- | --- | --- |
| 1 | 91 | 143 |
| 2 | 0 | 229 |
| 3 | $1.5 \times 10^3$ | $2.46 \times 10^3$ |
| 4 | 44 | 600 |
| 5 | $2.12 \times 10^3$ | $1.23 \times 10^4$ |
| 6 | $5 \times 10^4$ | $2.27 \times 10^4$ |
| 7 | $5 \times 10^4$ | $6.13 \times 10^4$ |
| 8 | $1 \times 10^5$ | $2.08 \times 10^5$ |

What is claimed is:

1. A method for the detection of microorganisms in a body fluid sample comprising mixing said body fluid sample with an enzyme in a buffer whereby components of said body fluid but substantially none of the microorganisms in said sample are lysed, staining said microorganisms with ethidium bromide and determining the presence of said microorganisms by detecting the fluorescence emitted by said ethidium bromide.

2. A method in accordance with claim 1 wherein said sample is selected from the group consisting of blood, urine, cerebrospinal fluid, synovial fluid and pleural fluid.

3. A method in accordance with claim 2 wherein said sample is blood.

4. A method in accordance with claim 2 wherein said sample is urine.

5. A method in accordance with claim 3 wherein said blood is pretreated with an anticoagulant.

6. A method in accordance with claim 1 wherein said enzyme comprises a protease having lipase and nuclease activity.

7. A method in accordance with claim 6 wherein said lysing agent is 5XLA.

8. A method in accordance with claim 6 wherein said lysing agent is Zierdt's reagent.

9. A method in accordance with claim 1 further comprising a growth step wherein said sample is added to a culture medium and said lysing is carried out by adding said lysing agent to said sample in said culture medium after an incubation period.

10. A method in accordance with claim 1 further comprising a growth step wherein said sample is added to a composition comprising a lysing agent and a culture medium and said staining is carried out after an incubation period.

11. A method for the detection of microorganisms in a body fluid sample comprising mixing said body fluid sample with an enzyme in a buffer whereby components of said body fluid but substantially none of the microorganisms in said sample are lysed, staining said microorganisms with a fluorescent dye, and determining the presence of said microorganisms by detecting the fluorescence emitted by said fluorescent dye.

12. A method in accordance with claim 11 further comprising the steps of
   (a) adding said body fluid sample to a culture medium to provide a mixture; and
   (b) incubating said mixture to provide a count of said microorganisms sufficient for said detection before said mixing.

13. A method in accordance with claim 11 further comprising the steps of:
   (a) adding the body fluid sample to a composition containing a culture medium and a lysing agent to provide a mixture; and
   (b) incubating said mixture to simultaneously provide a count of said microorganisms sufficient for said detection and lyse said components.

14. A method for the detection of microorganisms in a body fluid sample comprising the steps of:
   (a) mixing said body fluid sample with an enzyme in a buffer to provide a mixture wherein components of said body fluid but substantially none of the microorganisms are lysed;
   (b) incubating said mixture;
   (c) contacting said mixture with a staining composition comprising ethidium bromide and a staining buffer;
   (d) directing excitation light to said mixture; and
   (e) detecting the fluorescence emitted by said ethidium bromide.

15. A method in accordance with claim 14 wherein said staining buffer comprises sodium borate, ethylenediamine tetraacetic acid, formaldehyde and octylphenoxy polyethoxy ethanol in water.

16. A method in accordance with claim 14 wherein said fluorescence is detected microscopically.

17. A method in accordance with claim 14 wherein said fluorescence is detected with a fluorescence activated flow cytometer.

18. A method for the detection of microorganisms in a body fluid sample comprising the steps of:
   (a) mixing the body fluid sample with 5XLA lysing agent to provide a mixture wherein components of said body fluid but substantially none of the microorganisms are lysed;
   (b) incubating said mixture;
   (c) adding a staining buffer and ethidium bromide to said mixture; and
   (d) flowing said mixture through a fluorescence activated flow cytometer and detecting the fluorescence associated with the microorganisms in said mixture.

* * * * *